United States Patent [19]

Cavazza

[11] 4,272,549
[45] Jun. 9, 1981

[54] THERAPEUTICAL METHOD FOR THE TREATMENT OF CHRONIC URAEMIC PATIENTS UNDERGOING PERIODICAL HAEMODIALYSIS AND LIQUID COMPOSITION FOR DIALYSIS FOR USE IN SUCH A METHOD

[76] Inventor: Claudio Cavazza, 35, Via Marocco, 00144 Rome, Italy

[21] Appl. No.: 38,734

[22] Filed: May 14, 1979

[30] Foreign Application Priority Data

May 15, 1978 [IT] Italy ............................... 49355 A/78

[51] Int. Cl.$^3$ ............................................ A61K 31/205
[52] U.S. Cl. .................................................... 424/316
[58] Field of Search ......................................... 424/316

[56] References Cited

U.S. PATENT DOCUMENTS

| 3,822,344 | 7/1974 | Corker | 424/316 |
| 3,830,931 | 8/1974 | De Felice | 424/316 |
| 3,968,241 | 7/1976 | De Felice | 424/319 |

OTHER PUBLICATIONS

Chem. Abst. 79, 134706z (1973)–Oram et al.
Fritz et al.: Proc. Natl. Acad. Sci. U.S.A. 54, 1226 (1965).
Böhmer et al.: Clinica Chimica Acta. 57, 55 (1971).
Chen et al.: Clin. Chem. 23(2) 278 (1977).
Seccombe et al.: Biochim. Biophys. Acta. 528 483 (1978).
Bartel et al.: Fed. Proc. 37 445, Abs. 1239 (1978).
Böhmer et al.: Lancet 1978, 126.
Bizzi et al.: Biomedicine, 29 183 (1978).
Bizzi et al.: Lancet 1979, 882.

Primary Examiner—Douglas W. Robinson
Attorney, Agent, or Firm—Jacobs & Jacobs

[57] ABSTRACT

A therapeutical method for treating uraemic patients in regular dialysis treatment (RDT) is disclosed, wherein carnitine is administered to the patients. Carnitine can be administered over the whole treatment period by the oral route exclusively. Alternatively, while oral administration is carried out only in those days in which the patient is not subjected to dialysis, when the patient undergoes dialysis, a carnitine-containing dialyzing liquid is used. Furthermore, a suitable dialyzing solution is also disclosed.

12 Claims, No Drawings

THERAPEUTICAL METHOD FOR THE TREATMENT OF CHRONIC URAEMIC PATIENTS UNDERGOING PERIODICAL HAEMODIALYSIS AND LIQUID COMPOSITION FOR DIALYSIS FOR USE IN SUCH A METHOD

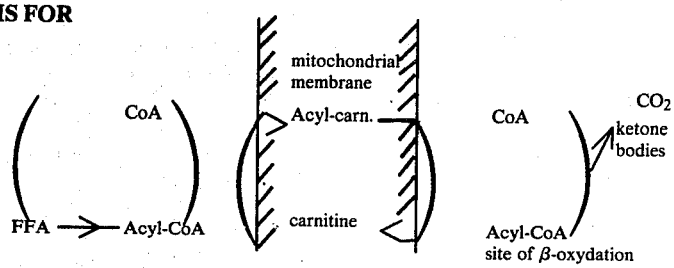

BACKGROUND OF THE INVENTION

1. Field of the Invention

The present invention pertains to a therapeutical method for the treatment of chronic uraemic patients submitted to haemodialysis and, more particularly, pertains to a therapeutical method compensating or preventing the depletion of carnitine which occurs in subjects affected by chronic uraemia undergoing periodical haemodialysis.

According to another aspect, the present invention pertains to a concentrated polysaline solution and a diluted polysaline solution, obtainable from the former by suitable dilution, adapted for use as the dialyzing liquid in the therapeutical method of the present invention.

2. Description of the Prior Art

It is known that patients affected by chronic uraemia, undergoing periodic haemodialysis, frequently develop myocardiopathies that are inalterable by intensive dialysis, and therefore not attributable to an accumulation of toxic catabolites nor to sodium and water retention. In such patients it is possible to observe a clinical picture known as post-dialytic syndrome, characterized by marked muscular asthenia and a sensation of torpor, particularly evident immediately following dialysis and which may often last even for several hours, so making difficult, if not impossible, a full resumption of working activity.

It has furthermore been found that while the plasma concentration of carnitine in uraemic patients prior to haemodialysis is equal to or slightly lower than the values observed in normal subjects, upon termination of dialysis the concentration of carnitine is reduced to approximately 25% of the pre-dialysis value. It has also been observed that during the period between the termination of one dialytic treatment and the beginning of the next the plasma concentration of carnitine tends to rise and practically reaches, within a few hours, its normal level, but this occurs due to the transfer of carnitine from the tissues to the plasma with attendant progressive tissue depletion. Particularly serious consequences are brought about by carnitine depletion in the myocardium and skeletal muscles.

In addition, it has been observed that there is a significant correlation between reduced carnitine concentration and increased free fatty acid levels in plasma which occur during haemodialysis. In fact, reduced carnitine concentration hinders normal cellular function thus reducing or blocking the oxidation of free fatty acids (FFA) which cannot reach the beta-oxidation sites since they do not cross the mitochondrial membrane as shown by the reaction scheme.

In such conditions there is a shortage of the principal energy supply to the muscular cells, especially the myocardial cells, which use fatty acid as their preferential energy substrate and develop the above-mentioned functional anomalies of the myocardium characterized by rhythm disturbances, contractile force disturbances, etc.

These affections are often encountered in patients submitted to periodical haemodialysis, such as to constitute one of the main risks when performing haemodialytic therapy.

SUMMARY OF THE INVENTION

Therefore it is apparent that the necessity has been felt for a suitable therapeutical means capable of compensating or preventing both the loss of carnitine in plasma during haemodialysis and the depletion of carnitine levels in tissues (particularly the myocardium and skeletal muscles) which occurs in subjects affected by chronic uraemia following periodical haemodialysis repeated over a prolonged period of time.

The object of the present invention is to provide such therapeutical means.

On the basis of the above, it would appear logical that the most efficacious method to compensate the loss of plasma carnitine which takes place in chronic uraemic patients during haemodialysis and the depletion of carnitine in tissues, resulting from repeated haemodialyses, consists in the intravenous administration of carnitine during the haemodialytic session.

This would be logically foreseen, especially since the most immediate and obvious lowering of the level of carnitine occurs in the plasma carnitine, with the maximum difference occuring between predialysis value and that revealed at the end of the dialysis session. In view of the relationship between loss and depletion of carnitine and the state of asthenia presented by the patient, the intravenous administration of carnitine would seem to be effective in counteracting also this state of asthenia.

Consequently, methods of carnitine administration other than the intravenous route would not seem to be able to furnish therapeutically efficacious results.

In accordance with the present invention however, a therapeutic method for the treatment of chronic uraemic patients under periodic haemodialysis has been discovered consisting in the oral administration to such patients, both during the days of haemodialysis session, and during the days between one session and another, of 3 to 6 g per day of carnitine or of any of its pharmaceutically acceptable salts.

Surprisingly, it has also been found that in some cases, if the administration of carnitine by the intravenous route in chronic uraemic patients is not carried out following the operating conditions which will be later described, the deep feeling of asthenia presented by such uraemic patients may be aggravated instead of alleviated. In some cases the occurrence of synaptic blockage has been noted, for the removal of which it has been necessary to administer prostigmine.

It was however found that the uraemic patient undergoing periodic haemodialytic treatment did not experience any discomfort and did not show any signs of asthenia when the administration by the intravenous route was effected by slow infusion during the haemodialytic session.

According to the invention the therapeutic method for treating chronic uraemic patients undergoing periodic haemodialysis, also includes therefore the following steps:

(1) during the days between one haemodialytic session and the next, administration to these patients of 3 to 6 g per day of carnitine, or any of its pharmaceutically acceptable salts, by the oral route;

(2) on the days of the haemodialytic session, administration to these patients, during the haemodialytic session, of 3 to 6 g of carnitine or any of its pharmaceutically acceptable salts, by slow infusion.

One the days of haemodialytic session, carnitine may also be administered partly by the oral route and partly by slow infusion. In this case, the overall quantity of carnitine administered shall not exceed approximately 10 g.

"Slow infusion" stands for an infusion in which the solution containing carnitine, or any of its pharmaceutically acceptable salts, is administered at the rate of 20 to 40 drops per minute.

The choice of a suitable solvent for carnitine, in view of the intended intravenous administration, would be evident for the expert. Normally, an accurately sterilised saline solution is used.

DESCRIPTION OF THE PREFERRED EMBODIMENT

It was also surprisingly found that particularly favourable therapeutic results were achieved by a method in which carnitine was administered by the oral route to the patient under haemodialytic treatment only on those days during which the patient was not submitted to a dialytic session, while during the actual dialytic session, a dialyzing liquid containing carnitine was used.

Such preferred therapeutic method, according to the invention, for the treatment of chronic uraemic patients undergoing haemodialysis, includes more particularly the following steps:

(1) on the days between one haemodialytic session and the next, administration by the oral route to these patients of 3 to 6 g per day of carnitine or any of its pharmaceutically acceptable salts;

(2) on the days of haemodialytic session, submission of these patients to dialysis using, as dialyzing liquid, a solution containing a quantity of carnitine or of any of its pharmaceutically acceptable salts, sufficient to make a molar concentration of carnitine in the said solution at least equal to the molar concentration of the plasma carnitine of the patient under dialytic treatment.

It was found that by operating in such a manner, it is possible to avoid the loss of plasma carnitine which otherwise takes place during a haemodialytic session, the concentration of plasma carnitine remaining practically unchanged during the dialytic session.

In this manner, it is possible to avoid the tissue carnitine depletion which is the long-term consequence of repeated losses of carnitine the patient undergoes during the successive dialytic sessions he is submitted to over a prolonged period of time.

Although for this purpose it is sufficient that the solution for the haemodialysis be equimolar in carnitine which respect to the blood of the patient under dialytic treatment, it is preferable to operate with a slightly more concentrated solution.

In practice, the haemodialysis solution contains 50 to 100, preferably 60–80 $\mu$ moles/liter of carnitine or of any of its pharmaceutically acceptable salts.

A polysaline solution, ready for use in the dialytic treatment of chronic uraemic patients, contains:

| | |
|---|---|
| sodium ions | 140–145 m Eq/l |
| potassium ions | 0.8–1.2 m Eq/l |
| calcium ions | 3.2–3.8 m Eq/l |
| magnesium ions | 1.2–1.8 m Eq/l |
| chlorine ions | 105–115 m Eq/l |
| acetic ions | 35–40 m Eq/l |
| glucose | 0.97–1.03 m Eq/l |
| carnitine | 50–100 $\mu$M/l |

As is known in the haemodialytic technique, concentrated polysaline solutions are available commercially which when suitably diluted provide solutions ready for use.

In accordance with the invention, a concentrated polysaline solution for haemodialysis includes a quantity of carnitine or of any of its pharmaceutically acceptable salts, sufficient, upon dilution of this solution, to give a dilute polysaline solution ready for use where the carnitine molar concentrations is at least equal to the molar concentration of the plasma carnitine of the patient under dialytic treatment.

As an example—a concentrated plysaline solution, a liter of which diluted with 34 liters of distilled water gives a solution ready for use, has the following typical composition:

| | |
|---|---|
| sodium chloride | 210–215 g/l |
| sodium acetate trihydrate | 178–182 g/l |
| magnesium chloride hexahydrate | 4.8–5.5 g/l |
| calcium chloride hexahydrate | 12.5–14 g/l |
| potassium chloride | 2.5–2.7 g/l |
| anhydrous glucose | 34–36 g/l |
| carnitine | 1750–3500 $\mu$M/l |

Clinical tests have been performed, submitting chronic uraemic patients to carnitine treatment according to the present invention. Some clinical cases are subsequently illustrated. A first group of patients (Group A: 5 patients) was treated with placebo for 30 days. A second group of patients (Group B: 5 patients) was treated with carnitine for 30 days according to the wholly oral administration method.

A third group of patients (Group C: 4 patients) was treated with carnitine alternating the oral administration on the days in which the patients were not submitted to dialysis, with a haemodialytic treatment where carnitine was present in the dialysis liquid.

Finally a fourth group of patients (Group D: 8 patients) was treated with carnitine alternating the oral administration, in the days in which they were not submitted to dialysis, with a slow infusion during the haemodialytic session.

The following tests were carried out of the patients of Group A and B (before and after treatment):

(a) electrocardiogramme
(b) maximal effort test with a cicloergometer

A computerized Dynavit cicloergometer was used which provides the load (in watts) to which the patient must be submitted, based on body weight and age.

The trial was interrupted either for muscular exhaustion or for over-reaching of the cardiac frequency limits (> H.R.) (this parameter also established by the cicloergometer computer).

(c) neuromuscular conduction rate (NMCR)
(d) electromyography (EMG)

This parameter was used in order to assing a precise scientific significance thus rendering measurable the subjective asthenic "sensation" so frequently experienced by patients undergoing periodic haemodialytic treatment.

The measurements of neuromuscular conduction rate and of the electromyography were carried out with MK III Medelek apparatus.

For the interpretation of the electromyography see for example:

Simpson, J. A.; "Control of Muscle in Health and Disease, in Control and Innervation of Skeletal Muscle"; (B. L. Andrew, (1966), p. 171-180), and Walton, J. N.; "Disorders of Voluntary Muscle"; Churchill Livingstone, 3rd edition, (1974) p. 1014-1019.

(e) cardiac diameter measurement.

GROUP A

CASE 1

A 53 year old female patient, diagnosed as suffering from chronic renal insufficiency due to chronic pyelonephritis, underwent regular dialysis treatment (3 sessions per week of 5 hours each).

Regular dialysis treatment commenced: Sept. 18, 1976.

A placebo was administered to the patient for 30 days.
ECG prior to therapy: within normal limits
ECG after therapy: within normal limits
Physical effort with 80 watt load
    prior to therapy: 0 min 38 seconds (muscle exhaustion)
    after therapy: 0 min 35 seconds (muscle exhaustion)
NMCR (neuromuscular conduction rate)
    prior to therapy: 38 m/sec
    after therapy: 38 m/sec
EMG (maximum effort)
    prior to therapy: single oscillations
    after therapy: single oscillations

| | Cardiac diameters | |
|---|---|---|
| | prior to | after |
| Type | therapy | |
| Longitudinal diameter | 15.0 | 15.1 |
| Basal diameter | 12.6 | 12.6 |
| Transversal diameter | 14.0 | 14.0 |
| Left ventricular chord | 8.5 | 8.5 |
| Left ventricular sagitta | 1.6 | 1.6 |
| Cardiothoracic index | 46% | 46% |

CASE 2

A 44 year old male patient, diagnosed as suffering from chronic renal insufficiency due to renal TB, underwent regular dialysis treatment (3 sessions per week of 3.5 hours each).

Regular dialysis treatment commenced: July 30, 1977
A placebo was administered to the patient for 30 days.
ECG prior to therapy: within normal limits
ECG after therapy: within normal limits
Physical effort with 70 watt load
    prior to therapy: 1 min 37 seconds (>HR)
    after therapy: 1 min 41 seconds (>HR)
NMCR (neuromuscular conduction rate)
    prior to therapy: 42 m/sec
    after therapy: 42 m/sec
EMG (maximum effort)
    prior to therapy: subinterferential
    after therapy: subinterferential

| | Cardiac diameters | |
|---|---|---|
| | prior to | after |
| Type | therapy | |
| Longitudinal diameter | 14.0 | 14.0 |
| Basal diameter | 11.4 | 11.4 |
| Transversal diameter | 13.3 | 13.3 |
| Left ventricular chord | 10.3 | 10.3 |
| Left ventricular sagitta | 1.8 | 1.8 |
| Cardiothoracic index | 46% | 46% |

CASE 3

A 65 year old male patient, diagnosed as suffering from chronic renal insufficiency due to renal TB, underwent regular dialysis treatment (3 sessions per week of 5 hours each).

Regular dialysis treatment commenced: June 4, 1977
A placebo was administered to the patient for 30 days.
ECG prior to therapy: left ventricular overload
ECG after therapy: left ventricular overload
Physical effort with 120 watt load
    prior to therapy: 2 min 28 seconds (muscular exhaustion)
    after therapy: 2 min 20 seconds (muscular exhaustion)
NMCR (neuromuscular conduction rate)
    prior to therapy: 40 m/sec
    after therapy: 40 m/sec
EMG (maximum effort)
    prior to therapy: subinterferential
    after therapy: subinterferential

| | Cardiac diameters | |
|---|---|---|
| | prior to | after |
| Type | therapy | |
| Longitudinal diameter | 16.4 | 16.2 |
| Basal diameter | 12.3 | 12.3 |
| Transversal diameter | 14.8 | 15.8 |
| Left ventricular chord | 10.2 | 10.3 |
| Left ventricular sagitta | 2.4 | 2.4 |
| Cardiothoracic index | 54% | 55% |

CASE 4

A 30 year old male patient, diagnosed as suffering from chronic renal insufficiency due to chronic glomerulonephritis, underwent regular dialysis treatment (3 sessions per week of 4 hours each).

Regular dialysis treatment commenced: Jan. 9, 1978

A placebo was administered to the patient for 30 days.

ECG prior to therapy: left ventricular overload
ECG after therapy: left ventricular overload
Physical effort with 60 watt load
    prior to therapy: 1 min 12 seconds (muscular exhaustion)
    after therapy: 1 min 01 seconds (muscular exhaustion)
NMCR (neuromuscular conduction rate)
    prior to therapy: 50 m/sec
    after therapy: 50 m/sec
EMG (maximum effort)
    prior to therapy: interferential
    after therapy: interferential

| | Cardiac diameters | |
|---|---|---|
| | prior to | after |
| Type | therapy | |
| Longitudinal diameter | 14.6 | 14.6 |
| Basal diameter | 11.5 | 11.5 |
| Transversal diameter | 14.0 | 14.0 |
| Left ventricular chord | 9.8 | 9.8 |
| Left ventricular sagitta | 1.8 | 1.8 |
| Cardiothoracic index | 45% | 45% |

CASE 5

A 41 year old female patient, diagnosed as suffering from chronic renal insufficiency due to nephroangiosclerosis, underwent regular dialysis treatment (3 sessions per week of 4 hours each).

Regular dialysis treatment commenced: Sept. 27, 1977

A placebo was administered to the patient for 30 days.

ECG prior to therapy: left ventricular overload
ECG after therapy: left ventricular overload
Physical effort with 60 watt load
    prior to therapy: 2 min 32 seconds (>HR)
    after therapy: 2 min 30 seconds (>HR)
NMCR (neuromuscular conduction rate)
    prior to therapy: 52 m/sec
    after therapy: 50 m/sec
EMG (maximum effort)
    prior to therapy: subinterferential
    after therapy: subinterferential

| | Cardiac diameters | |
|---|---|---|
| | prior to | after |
| Type | therapy | |
| Longitudinal diameter | 15.3 | 15.2 |
| Basal diameter | 12.1 | 12.0 |
| Transversal diameter | 14.4 | 14.4 |
| Left ventricular chord | 10.2 | 10.2 |
| Left ventricular sagitta | 1.6 | 1.6 |
| Cardiothoracic index | 52% | 52% |

GROUP B

CASE 1

A 26 year old male patient, diagnosed as suffering from chronic renal insufficiency due to chronic glomerulonephritis, underwent regular dialysis treatment (3 sessions per week of 5 hours each).

Regular dialysis treatment commenced: Jan. 14, 1978

Carnitine (3 g/day) was administered to the patient for 30 days.

ECG prior to therapy: initial left ventricular overload
ECG after therapy: initial left ventricular overload
Physical effort with 60 watt load
    prior to therapy: 2 min 01 seconds (muscular exhaustion)
    after therapy: 4 min 18 seconds (muscular exhaustion)
NMCR (neuromuscular conduction rate)
    prior to therapy: 50 m/sec
    after therapy: 50 m/sec
EMG (maximum effort)
    prior to therapy: interferential
    after therapy: interferential

| | Cardiac diameters | |
|---|---|---|
| | prior to | after |
| Type | therapy | |
| Longitudinal diameter | 15.7 | 15.4 |
| Basal diameter | 13.0 | 12.6 |
| Transversal diameter | 14.5 | 14.1 |
| Left ventricular chord | 13.2 | 12.6 |
| Left ventricular sagitta | 1.5 | 1.5 |
| Cardiothoracic index | 51% | 49% |

CASE 2

A 58 year old female patient, diagnosed as suffering from chronic renal insufficiency due to polycystic kidney, underwent regular dialysis treatment (3 sessions per week of 4.5 hours each).

Regular dialysis treatment commenced: Aug. 3, 1977

Carnitine (5 g/day) was administered to the patient for 30 days.

ECG prior to therapy: bordering normal limits
ECG after therapy: bordering normal limits
Physical effort with 70 watt load
    prior to therapy: 2 min 00 seconds (muscular exhaustion)
    after therapy: 3 min 18 seconds (muscular exhaustion)
NMCR neuromuscular conduction rate)
    prior to therapy: 49 m/sec
    after therapy: 50 m/sec
EMG (maximum effort)
    prior to therapy: subinterferential
    after therapy: interferential

| | Cardiac diameters | |
|---|---|---|
| | prior to | after |
| Type | therapy | |
| Longitudinal diameter | 13.2 | 13.0 |
| Basal diameter | 9.6 | 9.6 |
| Transversal diameter | 13.9 | 13.7 |
| Left ventricular chord | 7.8 | 7.7 |
| Left ventricular sagitta | 1.1 | 1.1 |
| Cardiothoracic index | 55% | 54% |

CASE 3

A 70 year old male patient, diagnosed as suffering from chronic renal insufficiency due to chronic pielonephritys, underwent regular dialysis treatment (3 sessions per week of 4 hours each).

Regular dialysis treatment commenced: Apr. 26, 1977
Carnitine (6 g/day) was administered to the patient for 30 days.
ECG prior to therapy: subendocardial ischemia
ECG after therapy: subendocardial ischemia
Physical effort with 80 watt load
    prior to therapy: 1 min 06 seconds (>HR)
    after therapy: 1 min 46 seconds (>HR)
NMCR (neuromuscular conduction rate)
    prior to therapy: 37 m/sec
    after therapy: 40 m/sec
EMG (maximum effort)
    prior to therapy: single oscillations
    after therapy: subinterferential

| Type | Cardiac diameters prior to therapy | after therapy |
|---|---|---|
| Longitudinal diameter | 16.6 | 16.0 |
| Basal diameter | 12.6 | 12.0 |
| Transversal diameter | 15.0 | 14.7 |
| Left ventricular chord | 8.5 | 8.3 |
| Left ventricular sagitta | 1.5 | 1.5 |
| Cardiothoracic index | 45% | 44% |

CASE 4

A 62 year old female patient, diagnosed as suffering from chronic renal insufficiency due to chronic glomerulonephritis underwent regular dialysis treatment (3 sessions per week for 4 hours each).

Regular dialysis treatment commenced: Nov. 14, 1977
Carnitine (4 g/day) was administered to the patient for 30 days.
ECG prior to therapy: left ventricular overload
ECG after therapy: left ventricular overload
Physical effort with 50 watt load
    prior to therapy: 0 min 55 seconds (>HR)
    after therapy: 1 min 25 seconds (>HR)
NMCR (neuromuscular conduction rate)
    prior to therapy: 49 m/sec
    after therapy: 49 m/sec
EMG (maximum effort)
    prior to therapy: single oscillations
    after therapy: subinterferential

| Type | Cardiac diameters prior to therapy | after therapy |
|---|---|---|
| Longitudinal diameter | 14.6 | 14.2 |
| Basal diameter | 10.0 | 10.0 |
| Transversal diameter | 13.9 | 13.8 |
| Left ventricular chord | 9.0 | 9.0 |
| Left ventricular sagitta | 1.0 | 1.0 |
| Cardiothoracic index | 61% | 60% |

CASE 5

A 49 year old female patient, diagnosed as suffering from chronic renal insufficiency due to chronic glomerulonephritis, underwent regular dialysis treatment (3 sessions per week of 5 hours each).

Regular dialysis treatment commenced: Aug. 8, 1977
Carnitine (3 g/day) was administered to the patient for 30 days.
ECG prior to therapy: mild left ventricular myocardiopathy
ECG after therapy: mild left ventricular myocardiopathy
Physical effort with 100 watt load
    prior to therapy: 0 min 35 seconds (muscular exhaustion)
    after therapy: 1 min 05 seconds (muscular exhaustion)
NMCR (neuromuscular conduction rate)
    prior to therapy: 48 m/sec
    after therapy: 48 m/sec
EMG (maximum effort)
    prior to therapy: subinterferential
    after therapy: interferential

| Type | Cardiac diameters prior to therapy | after therapy |
|---|---|---|
| Longitudinal diameter | 16.7 | 16.3 |
| Basal diameter | 12.1 | 11.7 |
| Transversal diameter | 15.9 | 14.8 |
| Left ventricular chord | 11.6 | 11.4 |
| Left ventricular sagitta | 2.3 | 2.1 |
| Cardiothoracic index | 55% | 51% |

GROUP C

Four patients (suffering from chronic renal insufficiency) underwent the following treatment:

on the days between the dialysis sessions, 3 g/day of carnitine were orally administered to the patients;

the patients underwent three dialysis sessions per week, using a polysaline dialyzing solution comprising 65 μmoles/l of carnitine. A coil kidney dialyser 5 Dialiyx SP 1052 Dasco (Modena, Italy) was used.

The plasma carnitine levels were measured before, after dialysis and 6 hours later.

The same four patients were subsequently treated by subjecting them to the normal 3 dialysis sessions weekly, without any administration of carnitine (either orally or in the dialyzing solution).

The results obtained are summarized in Table 1.

TABLE 1

Effect of carnitine added to the dialyzing solution on the plasma carnitine concentrations of patients under haemodialysis.

| added to dialyzing solution | PLASMA CARNITINE | | | | | |
|---|---|---|---|---|---|---|
| | TOTAL | | | FREE | | |
| | before | after | 6 hours later | before | after | 6 hours later |
| no addition | 45 ± 3 | 21 ± 1* | 40 ± 2 | 28 ± 2 | 7 ± 1* | 24 ± 1 |
| Carnitine 65 | 50 ± 3 | 47 ± 7 | 49 ± 4 | 33 ± 5 | 32 ± 3 | 35 ± 2 |

*$p < 0.01$ compared to the level before treatment
Average of 4 patients

GROUP D

Eight patients underwent haemodialysis twice a week (4 hours each session) having had carnitine therapy at the following doses:

on the days of dialysis: 2 g by the oral route 2 hours prior to dialysis; 6 g by slow infusion for 1 hour, 1 hour before dialysis termination; 2 g by the oral route, 4 hours after dialysis termination;

during the following days: 2 g by the oral route 3 times per day.

Another group of eight patients also under haemodialysis and received no therapy.

At established times plasma levels of total carnitine and F.F.A. were measured.

The results are reported in Table 2 and clearly indicate that the carnitine treatment maintains an equilibrium in the values of both parameters.

A remarkable improvement in cardiac function was also observed, showing an obvious reduction and in some cases the disappearance, of rythym disturbances. Absence of post-dialysis asthenia.

TABLE 2

Effect of carnitine administration by slow infusion on the plasma carnitine and FFA levels. N = 8 cases.

|  | Placebo | Carnitine | Placebo | Carnitine |
|---|---|---|---|---|
|  | Carnitine $\mu M$ | | FFA $\mu Eq/l$ | |
| 6 hours before haemodialysis | 103.4 ± 12.4 | 98.5 ± 12.3 | 0.35 ± 0.064 | 0.37 ± 0.071 |
| at the beginning of session | 98.5 ± 12.4 | 120.5 ± 15.4 | 0.34 ± 0.064 | 0.36 ± 0.080 |
| 2 hours after beginning of session | 34.3 ± 8 | 90.4 ± 6 | 0.84 ± 0.072 | 0.38 ± 0.075 |
| at the end of session | 16.5 ± 6 | 88.3 ± 10 | 1.58 ± 0.080 | 0.40 ± 0.063 |
| 4 hours after the end of session | 40.3 ± 12 | 82.4 ± 9 | 1.52 ± 0.066 | 0.45 ± 0.057 |
| 24 hours after the end of session | 65.4 ± 15 | 95.2 ± 12 | 0.85 ± 0.058 | 0.40 ± 0.093 |
| 48 hours after the end of session | 75.5 ± 14 | 99.4 ± 15 | 0.40 ± 0.063 | 0.38 ± 0.066 |

What is claimed is:

1. A method for alleviating asthenia and muscle weakness in a chronic uraemic patient under regular dialysis treatment, which comprises submitting said patient to dialysis with a polysaline dialytic solution which contains a quantity of carnitine, or a pharmaceutically acceptable salt thereof, sufficient to render the molar concentration of carnitine in said solution at least equal to the molar concentration of the plasma carnitine of the patient under dialytic treatment.

2. The method according to claim 1 wherein the concentration of carnitine in said dialytic solution is substantially equimolar to the concentration of carnitine in the plasma of said patient.

3. The method according to claim 1 wherein the concentration of carnitine in said dialytic solution is from 50 mole to 100 $\mu$mole per liter of solution.

4. The method according to claim 1 wherein there is administered to said uraemic patient on the day of said haemodialysis from 3 to 6 grams of carnitine or an equivalent amount of a pharmaceutically acceptable salt thereof.

5. The method according to claim 4 wherein said carnitine is administered orally.

6. The method according to claim 4 wherein said carnitine is administered by slow infusion.

7. The method according to claim 1 wherein from 3 to 6 grams of carnitine or an equivalent amount of a pharmaceutically acceptable salt thereof is orally administered to said patients on days between haemodialysis from 3 to 6 grams of carnitine/day or an equivalent amount of a pharmaceutically acceptable salt thereof.

8. A polysaline dialytic solution for use in the dialysis of chronic uraemic patients which contains, per liter of solution, from 140 to 145 mEq of sodium ions, from 0.8 to 1.2 mEq of potassium ions, from 3.2 to 3.8 mEq of calcium ions, from 1.2 to 1.8 mEq of magnesium ions, from 35 to 40 mEq of chloride ions, from 0.95 to 1.05 mEq of glucose and from 50 to 100 $\mu$moles of carnitine or a pharmaceutically acceptable salt thereof.

9. In a polysaline haemodialysis solution concentrate the improvement which consists of an amount of carnitine or a pharmaceutically acceptable salt thereof sufficient, upon dilution of said concentrate to produce a ready-for-use polysaline haemodialysis solution, with a carnitine molar concentration at least equal to the molar concentration of the plasma carnitine of the patient under dialytic treatment.

10. The concentrate according to claim 9 wherein the amount of carnitine or a pharmaceutically acceptable salt thereof is sufficient, upon said dilution, to yield a concentration of carnitine equimolar to that in the blood of the patient under dialytic treatment.

11. The concentrate according to claim 9 wherein the amount of carnitine or a pharmaceutically acceptable salt thereof is sufficient, upon said dilution, to yield a carnitine concentration of from 50 to 100 $\mu$moles/liter.

12. The concentrated solution of claim 11, comprising:

| | |
|---|---|
| sodium chloride | 210–215 g/l |
| sodium acetate trihydrate | 178–182 g/l |
| magnesium chloride hexahydrate | 4.8–5.5 g/l |
| calcium chloride hexahydrate | 12.5–14 g/l |
| potassium chloride | 2.5–2.7 g/l |
| anhydrous glucose | 34–36 g/l |
| carnitine or pharmaceutically acceptable salt thereof | 1750–3500 $\mu$moles/l |

* * * * *